United States Patent
Doyle et al.

(10) Patent No.: US 8,137,705 B2
(45) Date of Patent: Mar. 20, 2012

(54) **CONTROL OF ENTEROHEMORRHAGIC *E. COLI* IN FARM ANIMAL DRINKING WATER**

(75) Inventors: Michael P. Doyle, Peachtree City, GA (US); Tong Zhao, Peachtree City, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1147 days.

(21) Appl. No.: 11/883,425

(22) PCT Filed: Jan. 25, 2006

(86) PCT No.: PCT/US2006/002467
§ 371 (c)(1),
(2), (4) Date: Nov. 28, 2007

(87) PCT Pub. No.: WO2006/083622
PCT Pub. Date: Aug. 10, 2006

(65) Prior Publication Data
US 2008/0166430 A1    Jul. 10, 2008

Related U.S. Application Data

(60) Provisional application No. 60/648,885, filed on Feb. 1, 2005.

(51) Int. Cl.
| | |
|---|---|
| *A01N 59/06* | (2006.01) |
| *A01N 37/06* | (2006.01) |
| *A01N 37/02* | (2006.01) |
| *A61K 33/06* | (2006.01) |
| *A61P 31/04* | (2006.01) |
| *A01P 1/00* | (2006.01) |

(52) U.S. Cl. .................. 424/696; 514/557; 514/558
(58) Field of Classification Search .................. 424/696; 514/557, 558
See application file for complete search history.

(56) References Cited

FOREIGN PATENT DOCUMENTS
WO    WO99/44444    9/1999

OTHER PUBLICATIONS

International Search Report and Written Opinion for PCT/US2006/002467 filed Jan. 25, 2006.
Zhao.T. "Influence of Freezing and Freezing Plus AcidicCalcium Sulfate and Lactic Acid Addition on Thermal Inactivation of *Escherichia coli* O157:H7 in Ground Beef," Database HCAPLUS on STN, Chemical Abstracts Service, Journal of Food Protection, 2004:731159, (2004).
Marshall, R.T. "Acids Pathogens, Foods and Us' Abstract, Food Protection Trends," Database CABA on STN, CABI Publishing 2003, No. 2004:10551, (2003).
Annamalai, T. "In Vitro Inactivation of *Escherichia coli* O157:H7 in Bovine Rumen Fluid by Caprylic Acid," Database HCAPLUS on STN, Chemical Abstracts Service, Journal of Food Protection, 2004:473941, (2004).
Liu, X. "Experimental Observation on Factors Influencing Efficacy of Chlorine Dioxide in Killing Enterhemorrhagic *Escherichia coli* O154:H7 Abstract, Zhongguo Xiaoduxue Zazhi," Database HCAPLUS on STN, Chemical Abstracts Service, Journal of Food Protection, 1999:280152, (1999).
Lejeune, J.T. et al. "Livestock Drinking Water Microbiology and the Factors Influencing the Quality of Drinking Water Offered to Cattle," Database HCAPLUS on STN, Chemical Abstracts Service, Journal of Dairy Science, 2001:612994, (2001).
Zhao, T., et al., "Reduction of Carriage of Enterohemorrhagic *Escherichia coli* O157:H7 in Cattle by Inoculation With Probiotic Bacteria," Journal of Clinical Microbioloty, 1998, vol. 36, No. 3, pp. 641-647.
Brown, C., et al., "Experimental *Escherichia coli* O157:H7 Carriage in Calves," Applied and Environmental Microbiology, 1997, vol. 63, No. 1, pp. 27-32.

*Primary Examiner* — John Pak
(74) *Attorney, Agent, or Firm* — Thomas, Kayden, Horstemeyer & Risley, LLP

(57) ABSTRACT

The present invention relates to a new composition and methods for preventing the transmission of enterohemorrhagic *E. coli* and other foodborne pathogens to farm animals. In accordance with one embodiment, a composition comprising lactic acid and acidic calcium sulfate, and a compound selected from the group consisting of caprylic acid, sodium benzoate, butyric acid and chlorine dioxide is provided as an inhibitor of the growth of enterohemorrhagic *E. coli* and other foodborne pathogens.

7 Claims, No Drawings

CONTROL OF ENTEROHEMORRHAGIC *E. COLI* IN FARM ANIMAL DRINKING WATER

CROSS-REFERENCE TO RELATED APPLICATIONS

This application is a U.S. national application under 37 C.F.R. 371(b) of International Application Serial No. PCT/US2006/002467 filed Jan. 25, 2006, which claims priority under 35 USC §119(e) to U.S. Provisional Applications Ser. No. 60/648,885 filed Feb. 1, 2005, the disclosure of which is incorporated herein by reference.

BACKGROUND

Enterohemorrhagic *E. Coli* (EHEC), including strains O157:H7, O26:H11 and O111:NM have emerged in the last 10 years as important foodborne pathogens carried by farm animals such as cattle. Cattle constitute a major reservoir of EHEC and studies have revealed that contaminated drinking water is an important vehicle for transmission of the bacteria. An estimated 73,000 cases of *E. Coli* strain O157:H7 infections occur annually in the U.S. Cattle are a major reservoir and studies revealed that when present in cattle drinking water, *E. Coli* O157:H7 was disseminated to other cattle using the contaminated water source.

Genomic subtyping of *E. coli* O157:H7 isolates from farms by pulsed-field gel electrophoresis has revealed that a single O157:H7 strain is dominant among isolates from cohort and noncohort cattle, water, and other positive samples (i.e., from feed, flies, and a pigeon, etc.) on a farm. This indicates that drinking water is an important vehicle for disseminating *E. Coli* O157:H7 on the farm.

Studies indicate that once drinking water of farm cattle is contaminated with *E. coli* O157:H7, the bacterium is capable of surviving for extended periods of time. Sterilizing such EHEC contaminated drinking water is further complicated by the fact that such water frequently contains rumen contents or animal feces. A variety of treatments have been evaluated for their efficacy in killing *E. coli* O157:H7 in drinking water contaminated with cattle feces or rumen content. Results revealed that most had minimal effect on killing *E. coli* O157:H7 due at least in part to neutralization of the treatment by organic materials present in the rumen content or feces. Accordingly, there is a need for a practical treatment to eliminate or control *E. coli* O157:H7 in animal drinking water.

One aspect of the present disclosure is directed to a novel composition that will prevent or substantially reduce/eliminate the presence of enterohemorrhagic *E. coli* and other foodborne pathogens in farm animal drinking water.

SUMMARY OF VARIOUS EMBODIMENTS

The present disclosure is directed to compositions and methods for preventing the transmission of enterohemorrhagic *E. coli* and other foodborne pathogens to farm animals. In accordance with one embodiment a composition comprising lactic acid and acidic calcium sulfate, and a compound selected from the group consisting of caprylic acid, sodium benzoate, butyric acid and chlorine dioxide is provided as an inhibitor of the growth of enterohemorrhagic *E. coli* and other foodborne pathogens.

In accordance with one embodiment a method is provided for preventing or reducing the levels of enterohemorrhagic *E. coli* and other foodborne pathogens (including for example *Salmonella* and *Campylobacter*) present in the drinking water of animal, particularly in ungulate species. The method comprises adding an effective amount of an antimicrobial composition of the present invention to the drinking water. In one embodiment a method is provided for reducing the likelihood of transmission of enterohemorrhagic *E. coli* through drinking water in the trough on the farm, wherein the method comprises adding an effective amount of an antimicrobial composition to the drinking water, wherein the composition comprises lactic acid and acidic calcium sulfate, and a compound selected from the group consisting of caprylic acid, sodium benzoate, butyric acid and chlorine dioxide. In another embodiment a method of inhibiting the growth of enterohemorrhagic *E. coli* is provided wherein enterohemorrhagic *E. coli* are contacted with a composition comprising lactic acid and acidic calcium sulfate, and a compound selected from the group consisting of caprylic acid, sodium benzoate, butyric acid and chlorine dioxide.

DETAILED DESCRIPTION

Definitions

In describing and claiming the invention, the following terminology will be used in accordance with the definitions set forth below.

As used herein the term "enterohemorrhagic" relates to a class of intestinally-related organisms which causes colonic hemorrhaging and results in blood loss. These include members of the genus *Escherichia*, such as *E. coli* strains O157:H7, O26:H11 and O111:Nm.

As used herein the term "effective amount" means an amount sufficient to produce a selected effect. For example, an effective amount of an anti-microbial agent is an amount sufficient to kill >2 log *E. coli* O157:H7/ml within 30 min of contact, or effectively reduce a population of *E. coli* O157:H7 to undetectable levels by direct plating.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes alleviating the symptoms associated with a specific disorder or condition and/or preventing or eliminating said symptoms.

EMBODIMENTS

The present disclosure is directed to compositions and methods for preventing the transmission of pathogenic organisms to animals from contaminated communal drinking water. In one embodiment, an antibacterial composition is provided to decrease or eliminate the presence of enterohemorrhagic *E. coli, Salmonella* and/or *Campylobacter* strains in animal communal drinking water. Depending on initial cell numbers present, *E. coli* O157:H7 can survive at room temperature (21° C.) in water contaminated with rumen content for more than one year. Furthermore, many standard treatments that have anti-microbial activity are not practical for killing *E. coli* O157:H7 and other pathogenic organisms in farm drinking water because their antimicrobial activity is neutralized by the presence of organic material from rumen content or feces in the water. For example, the killing effect of 5 ppm chlorine and 22-24 ppm ozone was neutralized by the addition of rumen content at 100 parts water to 1 part or more of rumen content.

As described herein four chemical combinations have been found to be effective at killing large numbers of enterohemorrhagic *E. coli* present in drinking water sources, even in the presence of organic material from rumen content or feces in the water. More particularly, one embodiment is directed to an antimicrobial composition comprising lactic acid, acidic calcium sulfate and a third compound selected from the group consisting of caprylic (octanoic) acid, sodium benzoate, butyric acid and chlorine dioxide. Since these chemicals are combinations of organic acids, their concentrations are reported as volume/volume percentages. Typically, the pH of the anti-microbial compositions of the present disclosure ranges from about 2.0 to about 2.8. In accordance with one embodiment the composition comprises about 0.05% to about 1.0% lactic acid (about 4.7 to about 94 mM), about 0.3% to about 2.0% acidic calcium sulfate (about 15 to about 100 mN) and a further compound selected from the group consisting of about 25 to about 150 ppm chlorine dioxide, about 0.05% to about 1.0% caprylic acid (3.467 to about 69.34 mM), about 0.05 to about 0.2% sodium benzoate (about 3.45 to about 13 mM) and about 0.05 to about 1.0% butyric acid (about 5.67 to about 113.4 mM).

This composition can be added directly to the drinking water of farm animals to reduce or eliminate the presence of enterohemorrhagic *E. coli* and other pathogenic organisms in drinking water, even when the water is contaminated with organic material from rumen content or feces in the water. Concentrated antimicrobial/antibacterial formulations of the present compositions can be prepared for dilution in the animal drinking water to provide an effective final concentration of the final product. Accordingly, the present disclosure encompasses 2×, 3×, 5×, 10×, 20×, 100× and 200× concentrated formulations of the effective antimicrobial compositions of the present disclosure.

In accordance with one embodiment an effective anti-microbial composition comprises at least 0.05% lactic acid, at least 0.3% acidic calcium sulfate and at least 10 ppm chlorine dioxide. In one embodiment the composition comprises about 0.05 to about 1.0% lactic acid, about 0.3% to about 2.0% acidic calcium sulfate and about 25 to about 150 ppm chlorine dioxide. In an alternative embodiment the composition comprises at least 0.05% lactic acid, at least 0.3% acidic calcium sulfate and at least 0.05% caprylic acid. More particularly, in one embodiment the composition comprises about 0.05 to about 1.0% lactic acid, about 0.3% to about 2.0% acidic calcium sulfate and about 0.05 to about 0.1% caprylic acid. In another embodiment the composition comprises at least 0.05% lactic acid, at least 0.3% acidic calcium sulfate and at least 0.05% sodium benzoate. More particularly, in one embodiment the composition comprises about 0.05 to about 1.0% lactic acid, about 0.3% to about 2.0% acidic calcium sulfate and about 0.05 to about 0.2% sodium benzoate. In another embodiment the composition comprises at least 0.05% lactic acid, at least 0.3% acidic calcium sulfate and at least 0.05% butyric acid. In one particular embodiment the composition comprises about 0.05 to about 1.0% lactic acid, about 0.3% to about 2.0% acidic calcium sulfate and about 0.05 to about 1.0% butyric acid.

In a further embodiment an effective antimicrobial composition is provided comprising about 0.05 to about 1.0% lactic acid, about 0.3% to about 2.0% acidic calcium sulfate and two or more compounds selected from the group consisting of about 25 to about 150 ppm chlorine dioxide, about 0.05 to about 1.0% caprylic acid, about 0.05 to about 0.2% sodium benzoate and about 0.05 to about 1.0% butyric acid. In one embodiment the composition comprises about 0.05 to about 1.0% lactic acid, about 0.3% to about 2.0% acidic calcium sulfate, about 0.05 to about 0.2% sodium benzoate and about 0.05 to about 1.0% butyric acid. In another embodiment the composition comprises about 0.05 to about 1.0% lactic acid, about 0.3% to about 2.0% acidic calcium sulfate, about 0.05 to about 1.0% caprylic acid, and about 0.05 to about 1.0% butyric acid. In another embodiment the composition comprises about 0.05 to about 1.0% lactic acid, about 0.3% to about 2.0% acidic calcium sulfate, about 0.05 to about 1.0% caprylic acid and about 0.05 to about 0.2% sodium benzoate. In another embodiment the composition comprises about 0.05 to about 1.0% lactic acid, about 0.3% to about 2.0% acidic calcium sulfate, about 0.05 to about 1.0% caprylic acid, about 0.05 to about 0.2% sodium benzoate and about 0.05 to about 1.0% butyric acid. In another embodiment the composition comprises about 0.05 to about 1.0% lactic acid, about 0.3% to about 2.0% acidic calcium sulfate, about 0.05 to about 1.0% caprylic acid, about 0.05 to about 0.2% sodium benzoate, about 0.05 to about 1.0% butyric acid and about 25 to about 150 ppm chlorine dioxide.

In accordance with one embodiment a method is provided for decreasing enterohemorrhagic *E. coli* contamination of animal drinking water. In one embodiment the method is used to reduce or eliminate enterohemorrhagic *E. coli* contamination of farm animal drinking water, including the drinking water of ungulate species such as goats, sheep, pigs and cattle. The method comprises the steps of adding an effective amount of a composition comprising lactic acid, acidic calcium sulfate and a compound selected from the group consisting of caprylic acid, sodium benzoate, butyric acid and chlorine dioxide, to said drinking water. In accordance with one embodiment the composition is added in an amount to prepare a final concentration of about 0.05 to about 1.0% lactic acid, about 0.3% to about 2.0% acidic calcium sulfate, and one or more of the following: about 25 to about 150 ppm chlorine dioxide and/or about 0.05 to about 1.0% caprylic acid, and/or about 0.05 to about 0.2% sodium benzoate and/or about 0.05 to about 1.0% butyric acid in the drinking water.

In addition, the compositions of the present disclosure can be used to reduce or eliminate enterohemorrhagic *E. coli* or other pathogenic organisms (including *Salmonella* and *Campylobacter* strains) on the feeding and drinking containers and equipment as well as the drinking water itself. In accordance with one embodiment, the transmission of enterohemorrhagic *E. coli* to farm animals can be reduced by contacting the surfaces of feeding and watering containers and equipment on a regular basis with the anti-microbial compositions of the present disclosure. In one embodiment the watering containers can be emptied, contacted with the anti-microbial compositions of the present disclosure (at a predetermined concentration and length of time), optionally rinsed and refilled with water. Conducting this procedure on a regular basis (e.g. once a day or once every other day or once a week) is anticipated to eliminate or reduce transmission of enterohemorrhagic *E. Coli* to farm animals.

In addition, the compositions of the present disclosure can be used to reduce or eliminate enterohemorrhagic *E. coli* or other pathogenic organisms (including *Salmonella* and *Campylobacter* strains) on the surfaces of animal hides. In one embodiment the hides of animals can be contacted, by spraying, washing or other wise applying, with the anti-microbial compositions of the present disclosure (at a predetermined concentration and length of time) and optionally rinsed. In one embodiment the compositions can be applied to the animals in powderized form.

In accordance with one embodiment a method for inhibiting the transmission of enterohemorrhagic *E. coli* to farm animals comprises the steps of contacting farm feeding and watering equipment, or the external surfaces of the animals themselves, with a composition comprising lactic acid, acidic calcium sulfate and a compound selected from the group consisting of caprylic acid, sodium benzoate, butyric acid and chlorine dioxide. In one embodiment the composition comprises about 0.05 to about 1.0% lactic acid, about 0.3% to about 2.0% acidic calcium sulfate and a further compound selected from the group consisting of about 25 to about 150 ppm chlorine dioxide, about 0.05 to about 1.0% caprylic acid, about 0.05 to about 0.2% sodium benzoate and about 0.05 to about 1.0% butyric acid. In one embodiment the farm equipment is contacted with the composition by spraying the composition directly on the surface of the equipment.

In another embodiment of the present disclosure, a method of inhibiting the growth of an enterohemorrhagic *E. coli* and other pathogenic organisms is provided. The method comprises the step of contacting the pathogenic organism with a solution comprises about 0.05 to about 1.0% lactic acid, about 0.3% to about 2.0% acidic calcium sulfate and a further compound selected from the group consisting of about 25 to about 150 ppm chlorine dioxide, about 0.05 to about 1.0% caprylic acid, about 0.05 to about 0.2% sodium benzoate and about 0.05 to about 1.0% butyric acid.

The present disclosure further encompasses the use of the antimicrobial compositions of the present disclosure for the general disinfection and sterilization of any surface, including the surfaces of the animals themselves. In accordance with one embodiment the composition can be used to wipe down surfaces of equipment and instruments that come in contact with patients in a hospital as a means of reducing the incidence of nosocomial infection.

The antimicrobial compositions of the present disclosure can be used with other know anti-microbial agents to further enhance their efficacy against enterohemorrhagic *E. coli* and other pathogenic organisms. The antimicrobial compositions of the present disclosure may be used to reduce the average *E. coli* concentration in the drinking water of any farm animal. In accordance with one embodiment the composition is added to the drinking water of ungulate farm animal and in one specific embodiment the composition is added to the drinking water of cattle.

The following examples are intended only to further illustrate the invention and are not intended to limit the scope of the subject matter which is defined by the claims.

EXAMPLE 1

Materials and Methods

Bacterial Strains:

Five isolates of *E. coli* O157:H7, including 932 (human isolate), E009 (beef isolate), E0018 (cattle isolate), E0122 (cattle isolate), and E0139 (deer jerky isolate); five isolates of *E. coli* O26:H11, including strains DEC10E (cattle isolate), DEC9E (cattle isolate), DEC10B (cattle isolate), 3079-97 (human isolate), and 3183-96 (human isolate); and five strains of *E. coli* O111:NM, including strains 3208-95 (human isolate), 0944-95 (cattle isolate), 3287-97 (human isolate), 4543-95 (cattle isolate), and 0073-92 (cattle isolate) were used in this study. To facilitate the enumeration of these bacterial isolates, all strains of *E. coli* O26:H11, O111:NM, and O157:H7 were selected for resistance to nalidixic acid (50 µg/ml) according to the procedures reported previously (Brown, et al. (1997) Appl. Environ. Microbiol. 63:27-32, and Zhao, et al. (1998) J. Clin. Microbiol. 36:641-647). Each strain was grown individually in 10 ml of tryptic soy broth (TSB, Becton Dickinson Microbiology Systems, Sparks, Md.) containing 50 µg of nalidixic acid (Sigma Chemical Co., St. Louis, Mo.) per ml for 16-18 h at 37° C. with agitation (150 rpm).

The bacterial cells were sedimented and washed three times in 0.1 M phosphate-buffered saline, pH 7.2 (PBS) by centrifugation (4,000×g, 20 min), and resuspended in PBS. Cells were adjusted with PBS to an optical density at 640 nm of 0.5 (approximately $10^8$ CFU/ml). Five strains were combined at equal concentrations. The populations of each individual strain and the five-strain mixture were confirmed by enumeration on tryptic soy agar and Sorbitol MacConkey agar or MacConkey agar plates (TSA, SMA, and MCA, Becton Dickinson Microbiology Systems).

Survival characteristics of *E. coli* O157:H7 in drinking water containing different amounts of rumen content and held at different temperatures.

Tap water was mixed with a mixture of rumen content collected from three different beef cattle at a ratio of 100:1, 50:1, 25:1, 10:1, and 5:1 (ml:g), inoculated with a 5-strain mixture of ca. $10^6$ *E. coli* O157:H7/ml (high inoculum) or $10^3$ *E. coli* O157:H7 (low inoculum), and held at 8° C. or 21° C. A 1-ml sample was obtained at appropriate sampling times and serially diluted, and then 0.1 ml from each dilution was plated onto Sorbitol MacConkey agar containing 50 µg nalidixic acid/ml (SMA-NA) and incubated at 37° C. for 24 h. Colonies typical of *E. coli* O157:H7 (sorbitol-negative) were randomly picked for confirmation of *E. coli* by biochemical tests (API 20E miniaturized diagnostic test, bioMerieux Vitek, Hazelwood, Mo.) and for confirmation of serogroup O157 by latex agglutination assay (Oxoid, Ogdensburg, N.Y.). When *E. coli* O157:H7 was not detected by direct plating, a selective enrichment (TSB with 50 µg nalidixic acid/ml) at 37° C. for 24 h was applied. Isolates of *E. coli* O157:H7 obtained at the end of some studies were analyzed by pulsed-field gel electrophoresis analysis according to the method previously reported to identify the dominant surviving stain (Brown, et al. 1997).

Chlorine and Chlorine Dioxide Treatments

Standard chlorine solutions obtained from the HACH Company (Loveland, Colo.) were freshly diluted for each experiment in deionized water to the required concentration according to the method we reported before (Zhao, et al. 2001) J. Food Protect. 64:1607-1609). The concentration of free chlorine in diluted chlorine solutions was determined with a Digital Titrator (HACH Co.). The *E. coli* O157:H7 suspension (1 ml) was added to 199 ml rumen-contaminated water containing different concentration of chlorine solution (21° C.) being stirred with a magnetic stir bar in a 500-ml Erlenmeyer flask. At predetermined sampling times; 1.0 ml of the treated bacterial suspension was removed and mixed with 9.0 ml of neutralizing buffer (Becton Dickinson Microbiology Systems). Bacteria were serially (1:10) diluted in 0.1% peptone water and 0.1 ml of each dilution was surfaced-plated onto TSA-NA and SMA-NA in duplicate. The plates were held at 37° C. for 24 h and presumptive *E. coli* O157:H7 colonies were counted and confirmed by the methods described above. Studies with chlorine dioxide were conducted according to similar procedures. All studies were done in duplicate.

Treatment with Competitive Inhibition Bacteria

A mixture of five nalidixic-resistant strains of *E. coli* O157:H7 at $10^5$ cfu/ml and a mixture of three strains of competitive inhibition bacteria (*E. coli* #271, #786 and #797, Zhao, et al. 1998) antagonistic to *E. coli* O157:H7 at $10^7$ cfu/ml were inoculated into different flasks containing a mixture of water and rumen content at ratios of 100:1, 50:1, 25:1, 10:1, 5:1 and held at 21° C. A volume of 1 ml was removed daily or every other day and serially diluted in 0.1% peptone. A sample of 0.1 ml from each dilution was plated on the surface of SMA-NA plates in duplicate, and plates were incubated for 24 h at 37° C. Presumptive *E. coli* O157:H7 colonies were counted and confirmed by the methods described above. All studies were done in duplicate.

Ozone Treatments

Ozone was produced by an laboratory scale ozone generator (Model H-50, Hess Machine International, Ephrata, Pa.) equipped with an oxygen concentrator (Model AS-12, AirSep, Buffalo, N.Y.) and ozone concentrations (ppm) were measured by the indigo calorimeter method. Ozonated (22-24 ppm at 5° C.) water was mixed with rumen content at ratios of 100:1, 50:1, 25:1, 10:1, and 5:1. MilliQ water (Milli-Q Synthesis A10, Millipore Corp. Brillerica, Mass.) was used as the control. One ml of a mixture of 5 strains of *E. coli* O157:H7 ($10^8$ cfu) was mixed with 199 ml of the ozonated water with rumen content at 5° C. and sampled from 0 to 20 min. At each sampling time, 1 ml was removed, and immediately mixed with 9 ml of neutralizing buffer and serially (1:10) diluted and a volume of 0.1 ml from each dilution tube was plated on SMA-NA and TSA-NA plates in duplicate. Plates were incubated at 37° C. for 24 h. Presumptive *E. coli* O157:H7 colonies were counted and confirmed according to the method described above. All studies were done in duplicate.

Chemical Treatments

Chemicals, including lactic acid (0.05-0.5%, Fisher Scientific, Fair Lawn, N.J.), hydrogen peroxide (0.5%, Sigma Chemicals Inc. St. Louis, Mo.), sodium benzoate (0.1%, Fisher Scientific), acidic calcium sulfate (0.9-4.5%, Mionix Inc., Naperville, Ill.), caprylic acid (0.05-1.5%, Aldrich Chemicals Inc. Milwaukee, Wis.), butyric acid (0.5-4%, Aldrich Chemicals Inc), propionic acid (0.5-4%, Sigma Chemicals Inc.), and chlorine dioxide (10-1000 ppm, Aldrich Chemicals Inc.) were evaluated separately or as a combination. The chemicals were diluted to appropriate concentrations in MilliQ water (Milli-Q Synthesis A10, Millipore Corp.) initially tested with the pure cultures of *E. coli* O157:H7.

The effective chemical or combination of different chemicals was further tested for their killing effect on *E. coli* O157:H7 in tap water containing rumen content at different ratios. The 5-strain mixture of *E. coli* O157:H7 ($10^8$ cfu/ml) was added, held at 21° C. and sampled for up to 120 min. Following chemical treatment, 1.0-ml was immediately diluted (1:1) in neutralizing buffer, serially diluted in neutralizing buffer, and plated onto SMA-NA, TSA-NA and TSA plates in duplicate. The plates were incubated at 37° C. for 24 h for bacterial counts. When *E. coli* O157 was not detected by direct plating, a selective enrichment in TSB-NA was performed. Colonies growing on the surface of TSA-NA plates were counted as presumptive *E. coli* O157:H7. Presumptive colonies from the highest dilution were further confirmed as *E. Coli* by biochemical testing (API 20E miniaturized diagnostic test, bioMérieux Vitek, Hazelwood, Mo.) and O157 by a rapid agglutination assay (Oxoid, Ogdensburg, N.Y.).

Combinations of chemicals effective in killing *E. coli* O157:H7 were further evaluated in water containing a mixture of feces collected from three beef cattle at a ratio of 20:1 (ml:g) according to the methods described above for treatment in water containing rumen content. All effective chemical combinations were further evaluated for their killing effects on *E. coli* O26:H111 and O111:NM using the same protocol described for studies on *E. coli* O157:H7. All studies were done in duplicate or triplicate and results are reported as averages.

Results

Survival of *E. coli* O157:H7 in water contaminated with rumen content at 8° C. revealed that *E. Coli* O157:H7 inoculated at $10^6$ cfu/ml survived for 16, 6, 8, 3, and 5 weeks at tap water to rumen content ratios of 5:1, 10:1, 25:1, 50:1 and 100:1 (v/w), respectively. At 21° C., results revealed that *E. coli* O157:H7 inoculated at $10^6$ cfu/ml survived for 8, 15, 23, >56 and 24 weeks at water:rumen content ratios of 5:1, 10:1, 25:1, 50:1 and 100:1, respectively. Survival of *E. coli* O157:H7 was considerably greater at 21° C. than at 8° C. PFGE analysis of the isolates obtained at 56 weeks at 21° C. revealed that strains E0122 (cattle isolate) and E0139 (deer isolate) were the dominant survivors. These results indicate that drinking water for cattle could maintain *E. coli* O157:H7 for long periods of time and thereby serve as an important vehicle of transmission on the farm. Hence, effective and practical interventions to eliminate/control *E. coli* O157:H7 in drinking water for cattle are needed.

Treatment of *E. coli* O157:H7 with competitive inhibition *E. coli* in water containing rumen content decreased *E. coli* O157:H7 by 0.2 to 0.7 $\log_{10}$ cfu/ml by day 16 at 21° C. (Table 1), whereas *E. coli* O157:H7 increased by 0.6 to 1.0 $\log_{10}$ cfu/ml in the control (no competitive inhibition *E. coli*, Table 1). These results indicate that treatment of cattle drinking water with competitive inhibition *E. coli* controls growth of *E. coli* O157:H7 but has minimal effect on reducing *E. coli* O157:H7 populations. Hence, it is not an impactful approach for treating drinking water for cattle to control *E. coli* O157:H7.

Chlorine at 5 ppm in water immediately killed $10^6$-$10^7$ *E. coli* O157:H7/ml to reducing the bacteria to undetectable levels. However, the addition of rumen content to water at 100 parts water to 1 part rumen content or more (v/w) immediately neutralized the killing effect of free chlorine (Table 2).

Ozone at 22-24 ppm and 5° C. in water with no rumen content effectively killed $10^6$-$10^7$ *E. coli* O157:H7/ml (to undetectable level by direct plating method). However, adding rumen content to water at levels of 100 parts water to 1 part rumen content or more greatly decreased the antimicrobial activity of ozone (Table 3). Little to no *E. coli* O157:H7 inactivation occurred in 50 parts water to 1 part rumen content.

All chemicals, including lactic acid (0.05-0.5%), hydrogen peroxide (0.5%), sodium benzoate (0.1%), acidic calcium sulfate (0.9%), butyic acid (0.5-1.5%), propionic acid (0.5-4%), chlorine dioxide (10-100 ppm), and 0.05% caprylic acid, did not substantially reduce (<1.0 log/ml) *E. coli* O157:H7 within 20 min when tested individually in water containing rumen content (100:1) at 21° C. However, increasing the concentration of butyric acid to >2% and caprylic acid to >0.1% resulted in substantial inactivation of *E. coli* O157:H7 within 20 minutes (data not shown). However, these higher concentrations of butyric acid and caprylic acid were offensive to smell.

A variety of combinations of chemicals at different concentrations were subsequently evaluated for *E. coli* O157:H7 inactivation of more than 5 log cfu/ml within 20 min in water containing large amounts of rumen content (10:1). Three combinations, including: (A) 0.1% lactic acid, 0.9% acidic calcium sulfate and 0.05% caprylic acid; (B) 0.1% lactic acid, 0.9% acidic calcium sulfate and 0.1% sodium benzoate; and (C) 0.1% lactic acid, 0.9% acidic calcium sulfate and 0.5% butyric acid at 21° C. killed >5 log *E. coli* O157:H7/ml within 20 min in water containing rumen content at a ratio of 10:1 (v/w), (Table 4). A fourth chemical combination (D) containing 0.1% lactic acid, 0.9% acidic calcium sulfate and 100 ppm chlorine dioxide reduced *E. coli* O157:H7 populations by 2.6 log cfu/ml within 20 min and by 5.0 log within 120 min (Table 4).

These four chemical combinations were tested for their antimicrobial effect on *E. coli* O26:H111 and *E. coli* O111:NM in water containing large amounts of rumen content (10:1). Results revealed that three combinations (A, B and C) had the same antimicrobial activity (ca. 5 log reduction within 20 min at 21° C.) on *E. coli* O26:H111 (Table 5) and *E. coli* O111:NM except for Treatment B which required 30 min for a 5 log cfu/ml reduction (Table 6). Combination D reduced *E. coli* O26:H111 and *E. coli* O111:NM populations within 20 min by 4.3 and 3.0 log cfu/ml, respectively (Tables 5 and 6).

Further evaluation of these four chemical combinations on their antimicrobial activity to *E. coli* O157:H7, O26:H111 and O111:NM was determined in water containing cattle feces at a ratio of 20:1 (v/w). Results revealed that combinations A, B and C killed all three pathogens at 21° C. within 30 min (more than 5 log cfu/ml reduction; see Tables 4-6). Combination D reduced *E. coli* O157:H7, O26:H111 and O111:NM populations within 30 min by 3.5, 4.9, and 4.6 log cfu/ml, respectively (Tables 4-6).

TABLE 1

*E. coli* O157:H7 counts in water with rumen content at 21° C. treated with 3 strains of competitive inhibition *E. coli*

| Water:rumen content ratio | *E. coli* O157:H7 ($\log_{10}$ cfu/ml) at day: | | | | | | | |
|---|---|---|---|---|---|---|---|---|
| | 0 | 1 | 2 | 3 | 6 | 9 | 13 | 16 |
| 50:1 (control) | 3.5 | 4.6 | 5.5 | 4.8 | 5.8 | 5.7 | 5.5 | 4.1 |
| 50:1 (treatment) | 4.4 | 4.7 | 5.0 | 4.5 | 5.2 | 4.8 | 4.9 | 3.7 |
| 100:1 (control) | 3.4 | 4.8 | 5.4 | 5.5 | 5.9 | 5.7 | 5.5 | 4.4 |
| 100:1 (treatment) | 4.1 | 4.2 | 4.9 | 4.6 | 4.7 | 4.6 | 4.5 | 3.9 |

TABLE 2

*E. coli* O157:H7 counts in water with rumen content at 21° C. treated with 5 ppm chlorine

| Water:rumen content ratio | *E. coli* O157:H7 ($\log_{10}$ cfu/ml) at min: | | | | |
|---|---|---|---|---|---|
| | 0 | 1 | 5 | 10 | 20 |
| Water (control) | <1.7 | <1.7 | <1.7 | <1.7 | <1.7 |
| 100:1 | 5.6 | 5.6 | 5.6 | 5.8 | 5.6 |
| 50:1 | 7.2 | 7.0 | 7.1 | 7.0 | 7.1 |
| 25:1 | 6.4 | 6.5 | 6.6 | 6.5 | 6.5 |
| 10:1 | 6.4 | 6.4 | 6.6 | 6.7 | 6.7 |

TABLE 3

*E. coli* O157:H7 counts in water with rumen content at 5° C. treated with 22-24 ppm ozone

| Water:rumen content ratio | *E. coli* O157:H7 ($\log_{10}$ cfu/ml) at min: | | | | | |
|---|---|---|---|---|---|---|
| | 0 | 1 | 2 | 5 | 10 | 20 |
| 200:1 | <1.7 | <1.7 | <1.7 | <1.7 | <1.7 | <1.7 |
| 100:1 | 5.2 | 5.4 | 5.5 | 5.2 | 4.5 | 4.8 |
| 50:1 | 6.2 | 6.2 | 6.4 | 6.4 | 6.5 | 6.3 |
| 20:1 | 5.6 | 5.2 | 5.1 | 5.1 | 5.4 | 5.2 |
| Ozonated water only | <1.7 | <1.7 | <1.7 | <1.7 | <1.7 | <1.7 |
| Water only | 5.7 | 5.4 | 5.4 | 5.3 | 5.6 | 5.7 |

TABLE 4

*E. coli* O157:H7 counts in water containing rumen content (10:1, v/w) or feces (20:1, v/w) treated with different chemical combinations at 21° C.

| Treatment | *E. coli* O157:H7 counts ($\log_{10}$ cfu/ml) at min | | | | | | | |
|---|---|---|---|---|---|---|---|---|
| | 0 | 2 | 5 | 10 | 20 | 30 | 60 | 120 |
| Rumen content contamination | | | | | | | | |
| *E. coli* O157:H7 only (pH 8.2) | 6.2 | 6.1 | 6.1 | 6.0 | 5.9 | 5.9 | 6.1 | 5.9 |
| 0.1% lactic acid + 0.9% acidic calcium sulfate (pH 1.9) | 5.7 | 5.3 | 4.4 | 3.9 | 2.8 | 2.5 | 2.2 | 1.5 |
| 0.5% butyric acid (pH 4.0) | 5.9 | 5.9 | 5.9 | 5.8 | 5.7 | 5.8 | 5.6 | 5.7 |
| 0.05% caprylic acid (pH 7.8) | 6.0 | 6.0 | 6.0 | 5.9 | 6.0 | 5.9 | 5.9 | 6.0 |
| 0.1% sodium benzoate (pH 8.2) | 5.9 | 6.0 | 6.0 | 5.9 | 6.0 | 5.9 | 6.0 | 6.1 |
| 0.1% lactic acid + 0.9% acidic calcium sulfate + 0.5% butyric acid (pH 2.1) | 5.8 | 4.2 | +[a] | + | −[b] | − | − | − |
| 0.1% lactic acid + 0.9% acidic calcium sulfate + 0.1% sodium benzoate (pH 2.1) | 6.7 | 4.9 | 2.8 | 1.5 | − | − | − | − |
| 0.1% lactic acid + 0.9% acidic calcium sulfate + 0.05% caprylic acid (pH 2.0) | 5.2 | − | − | − | − | − | − | − |
| 0.1% lactic acid + 0.9% acidic calcium sulfate + 100 ppm chlorine dioxide (pH 2.1) | 5.7 | 4.3 | 3.7 | 3.4 | 3.1 | 2.9 | 2.1 | + |
| Fecal contamination | | | | | | | | |
| *E. coli* O157:H7 only (pH 8.5) | 6.1 | 6.1 | 6.1 | 6.0 | 6.1 | 6.1 | 6.1 | 6.2 |
| 0.1% lactic acid + 0.9% acidic calcium sulfate (pH 2.2) | 5.5 | 5.1 | 4.6 | 3.9 | 2.1 | 2.0 | 2.0 | 2.0 |
| 0.5% butyric acid (pH 4.5) | 6.0 | 6.0 | 6.0 | 6.1 | 6.1 | 6.1 | 6.0 | 6.0 |
| 0.05% caprylic acid (pH 7.1) | 6.0 | 5.6 | 4.3 | 2.3 | 2.0 | 2.0 | 2.0 | 1.7 |
| 0.1% sodium benzoate (pH 8.8) | 5.7 | 5.6 | 5.4 | 5.6 | 5.5 | 5.4 | 5.5 | 5.6 |
| 0.1% lactic acid + 0.9% acidic calcium sulfate + 0.5% butyric acid (pH 2.3) | 5.8 | 5.2 | 3.6 | 3.1 | 2.6 | + | + | + |
| 0.1% lactic acid + 0.9% acidic calcium sulfate + 0.1% sodium benzoate (pH 2.2) | 5.7 | 4.0 | 2.0 | 1.7 | + | + | − | − |
| 0.1% lactic acid + 0.9% acidic calcium sulfate + 0.05% caprylic acid (pH 2.2) | 4.9 | 2.0 | + | − | − | − | − | − |
| 0.1% lactic acid + 0.9% acidic calcium sulfate + 100 ppm chlorine dioxide (pH 2.3) | 5.5 | 3.0 | 2.7 | 2.5 | 2.5 | 2.0 | 1.7 | 1.7 |

[a]+, Positive by enrichment culture (<0.7 $\log_{10}$ cfu/ml)
[b]−, Negative by enrichment culture

TABLE 5

*E. coli* O26:H11 counts in water containing rumen content (10:1, v/w) or feces (20:1, v/w) treated with different chemical combinations at 21° C.

| Treatment | *E. coli* O26:H11 counts (log$_{10}$ cfu/ml) at min: | | | | | | | |
|---|---|---|---|---|---|---|---|---|
| | 0 | 2 | 5 | 10 | 20 | 30 | 60 | 120 |
| Rumen content contamination | | | | | | | | |
| *E. coli* O26:H11 only (pH 8.8) | 5.5 | 5.6 | 5.5 | 5.4 | 5.4 | 5.5 | 5.5 | 5.5 |
| 0.1% lactic acid + 0.9% acidic calcium sulfate (pH 2.2) | 5.0 | 4.4 | 3.7 | 3.2 | 2.4 | 2.3 | 1.8 | 1.0 |
| 0.5% butyric acid (pH 4.4) | 5.4 | 5.4 | 5.3 | 5.4 | 5.4 | 5.2 | 5.4 | 5.1 |
| 0.05% caprylic acid (pH 7.0) | 5.3 | 5.4 | 5.2 | 5.4 | 5.3 | 5.4 | 5.4 | 5.4 |
| 0.1% sodium benzoate (pH 8.6) | 5.6 | 5.5 | 5.4 | 5.5 | 5.5 | 5.5 | 5.4 | 5.5 |
| 0.1% lactic acid + 0.9% acidic calcium sulfate + 0.5% butyric acid (pH 2.3) | 5.3 | 4.1 | +[a] | + | −[b] | − | − | − |
| 0.1% lactic acid + 0.9% acidic calcium sulfate + 0.1% sodium benzoate (pH 2.3) | 5.2 | 5.1 | 3.6 | 1.7 | + | + | − | − |
| 0.1% lactic acid + 0.9% acidic calcium sulfate + 0.05% caprylic acid (pH 2.3) | 5.7 | − | − | − | − | − | − | − |
| 0.1% lactic acid + 0.9% acidic calcium sulfate + 100 ppm chlorine dioxide (pH 2.2) | 5.5 | 5.1 | 2.6 | 1.6 | 1.2 | 1.2 | + | + |
| Fecal contamination | | | | | | | | |
| *E. coli* O26:H11 only (pH 7.4) | 5.4 | 5.5 | 5.4 | 5.6 | 5.5 | 5.4 | 5.4 | 5.5 |
| 0.1% lactic acid + 0.9% acidic calcium sulfate (pH 2.1) | 5.4 | 4.7 | 4.7 | 4.5 | 4.0 | 2.0 | 1.9 | 1.5 |
| 0.5% butyric acid (pH 4.1) | 5.5 | 5.4 | 5.4 | 5.4 | 5.5 | 5.2 | 5.2 | 5.0 |
| 0.05% caprylic acid (pH 5.6) | 5.5 | 5.4 | 5.5 | 5.5 | 5.3 | 5.2 | 5.2 | 5.0 |
| 0.1% sodium benzoate (pH 7.8) | 5.5 | 5.4 | 5.5 | 5.4 | 5.5 | 5.4 | 5.5 | 5.4 |
| 0.1% lactic acid + 0.9% acidic calcium sulfate + 0.5% butyric acid (pH 2.1) | 5.4 | 3.3 | − | − | − | − | − | − |
| 0.1% lactic acid + 0.9% acidic calcium sulfate + 0.1% sodium benzoate (pH 2.1) | 5.3 | + | + | − | − | − | − | − |
| 0.1% lactic acid + 0.9% acidic calcium sulfate + 0.05% caprylic acid (pH 2.0) | 3.9 | 1.7 | − | − | − | − | − | − |
| 0.1% lactic acid + 0.9% acidic calcium sulfate + 100 ppm chlorine dioxide (pH 2.1) | 4.9 | 1.7 | + | + | + | − | − | − |

[a]+, Positive by enrichment culture (<0.7 log$_{10}$ cfu/ml)
[b]!, Negative by enrichment culture

TABLE 6

*E. coli* O111:NM counts in water containing rumen content (10:1, v/w) or feces (20:1, v/w) treated with different chemical combinations at 21° C.

| Treatment | *E. coli* O111:NM counts (log$_{10}$ cfu/ml) at min | | | | | | | |
|---|---|---|---|---|---|---|---|---|
| | 0 | 2 | 5 | 10 | 20 | 30 | 60 | 120 |
| Rumen content contamination | | | | | | | | |
| *E. coli* O111:NM only (pH 8.7) | 5.8 | 5.9 | 5.7 | 5.7 | 5.8 | 5.8 | 5.9 | 5.8 |
| 0.1% lactic acid + 0.9% acidic calcium sulfate (pH 2.2) | 5.5 | 5.4 | 4.2 | 2.3 | 2.1 | 2.0 | 1.6 | 1.0 |
| 0.5% butyric acid (pH 3.8) | 5.5 | 5.5 | 5.5 | 5.6 | 5.6 | 5.4 | 5.5 | 5.6 |
| 0.05% caprylic acid (pH 5.7) | 5.6 | 5.5 | 5.7 | 5.5 | 5.8 | 5.6 | 5.4 | 5.5 |
| 0.1% sodium benzoate (pH 8.6) | 5.6 | 5.6 | 5.5 | 5.6 | 5.6 | 5.5 | 5.4 | 5.5 |
| 0.1% lactic acid + 0.9% acidic calcium sulfate + 0.5% butyric acid (pH 2.3) | 5.7 | 5.0 | 2.8 | +[a] | + | −[b] | − | − |
| 0.1% lactic acid + 0.9% acidic calcium sulfate + 0.1% sodium benzoate (pH 2.3) | 5.7 | 5.3 | 4.4 | 3.6 | 2.1 | + | − | − |
| 0.1% lactic acid + 0.9% acidic calcium sulfate + 0.05% caprylic acid (pH 2.2) | 4.4 | + | + | − | − | − | − | − |
| 0.1% lactic acid + 0.9% acidic calcium sulfate + 100 ppm chlorine dioxide (pH 2.3) | 5.8 | 5.1 | 3.3 | 3.0 | 2.8 | 2.6 | 2.5 | 2.0 |
| Fecal contamination | | | | | | | | |
| *E. coli* O111:NM only (pH 7.7) | 5.6 | 5.7 | 5.7 | 5.6 | 5.6 | 5.6 | 5.7 | 5.7 |
| 0.1% lactic acid + 0.9% acidic calcium sulfate (pH 2.2) | 4.5 | 3.1 | 1.9 | 1.7 | 1.7 | 1.7 | 1.7 | 1.4 |
| 0.5% butyric acid (pH 4.1) | 5.6 | 5.6 | 5.5 | 5.6 | 5.6 | 5.6 | 5.6 | 5.6 |
| 0.05% caprylic acid (pH 5.5) | 5.7 | 5.5 | 5.7 | 5.5 | 5.6 | 5.7 | 5.5 | 5.4 |
| 0.1% sodium benzoate (pH 7.6) | 5.6 | 5.6 | 5.6 | 5.7 | 5.6 | 5.5 | 5.5 | 5.6 |
| 0.1% lactic acid + 0.9% acidic calcium sulfate + 0.5% butyric acid (pH 2.0) | 5.4 | 3.3 | − | − | − | − | − | − |
| 0.1% lactic acid + 0.9% acidic calcium sulfate + 0.1% sodium benzoate (pH 2.1) | 5.7 | 4.5 | 1.5 | − | − | − | − | − |
| 0.1% lactic acid + 0.9% acidic calcium sulfate + 0.05% caprylic acid (pH 2.0) | 5.5 | 2.3 | − | − | − | − | − | − |
| 0.1% lactic acid + 0.9% acidic calcium sulfate + 100 ppm chlorine dioxide (pH 2.0) | 5.3 | 2.7 | 2.6 | 1.9 | + | + | + | − |

[a]+, Positive by enrichment culture (<0.7 log$_{10}$ cfu/ml)
[b]!, Negative by enrichment culture

CONCLUSIONS

Drinking water for cattle and the surface of animal hides are important vehicles of *E. coli* O157:H7 transmission. Survival of *E. coli* O157:H7 in water contaminated with rumen content, at different water:rumen content, water:feces ratios, *E. coli* O157:H7 cell numbers, and temperatures, was determined. At 21° C., *E. coli* O157:H7 inoculated at a high inoculum (10$^{5.8}$ cfu/ml) survived for 8, 15, 23, >56 and 24 weeks and at a low inoculum (10$^{2.9}$ cfu/ml) survived for 8, 11, 10, 11 and 10 weeks at a water:ruinen content ratio of 5:1, 10:1, 25:1, 50:1 and 100:1, respectively.

Different treatments, including lactic acid, acidic calcium sulfate, chlorine, chlorine dioxide, hydrogen peroxide, caprylic acid, ozone, butyric acid, sodium benzoate and competitive inhibition *E. coli* were tested individually or in combination for inactivation of *E. coli* O157:H7 in the presence of rumen content. Chlorine (5 ppm) and ozone treatment (22-24 ppm at 5° C. or 8-12 ppm at 21° C.) of water had a minimal effect on killing *E. Coli* O157:H7 in the presence of rumen content at ratios of 50:1 and higher. Treatment by competitive inhibition *E. coli* in water with rumen content had minimal effect on *E. coli* O157:H7 counts compared with untreated controls.

Four chemical treatment combinations including: (a) 0.1% lactic acid (9.4 mM), 0.9% acidic calcium sulfate (45 mN) and 0.05% caprylic acid (3.467 mM), (Treatment A); b: 0.1% lactic acid (9.4 mM), 0.9% acidic calcium sulfate (45 mN) and 0.1% sodium benzoate (6.9 mM), (Treatment B); (c) 0.1% lactic acid (9.4 mM), 0.9% acidic calcium sulfate (45 mN) and 0.5% butyric acid (56.7 mM), (Treatment C); (d) 0.1% lactic acid (9.4 mM), 0.9% acidic calcium sulfate (45 mN) and 100 ppm chlorine dioxide (Treatment D) were highly effective at 21° C. in killing *E. Coli* O157:H7, O26: H11 and O111:NM/ml in water heavily contaminated with rumen content (ratio of 10:1 water:rumen content, v/w) or feces (ratio of 20:1, water:feces, v/w). Among them, Treatments A, B and C killed >5 $\log_{10}$ *E. coli* O157:H7, O26:H111 and O111:NM/ml within 30 min in water containing rumen content. For Treatment D, *E. coli* O157:H7, O26:H11, and O111:NM were reduced within 30 min by 2.8, 4.3, and 3.2 log cfu/ml in water containing rumen content, respectively, and by 3.5, 4.9, and 4.6 log cfu/ml in water with feces, respectively.

The invention claimed is:

1. An antimicrobial composition comprising about 0.1% lactic acid and about 0.9% acidic calcium sulfate, and a compound selected from the group consisting of: about 0.05% caprylic acid, and about 0.5% butyric acid.

2. A method of decreasing enterohemorrhagic *E. coli* contamination of animal drinking water, said method comprising adding an effective amount of a composition comprising about 0.1% lactic acid and about 0.9% acidic calcium sulfate, and about 0.05% caprylic acid or about 0.5% butyric acid, to said drinking water.

3. A method for inhibiting the transmission of enterohemorrhagic *E. coli* to farm animals, said method comprising the steps of contacting farm feeding and watering equipment with a composition comprising about 0.1% lactic acid and about 0.9% acidic calcium sulfate, and about 0.05% caprylic acid or about 0.5% butyric acid.

4. The method of claim 3 wherein the farm equipment is contacted once a day with said composition.

5. The method of claim 3 wherein the farm equipment is contacted with the composition by spraying the composition directly on the equipment.

6. A method for inhibiting the transmission of enterohemorrhagic *E. coli* to farm animals, said method comprising the steps of contacting the surface of said farm animal's hides with a composition comprising about 0.1% lactic acid and about 0.9% acidic calcium sulfate, and about 0.05% caprylic acid or about 0.5% butyric acid.

7. The method of claim 6 wherein the surface of said farm animal's hides is contacted with the composition by spraying the composition directly on the animal.

* * * * *